US012551360B2

(12) United States Patent
Gilmartin et al.

(10) Patent No.: US 12,551,360 B2
(45) Date of Patent: *Feb. 17, 2026

(54) STENT DELIVERY SYSTEM

(71) Applicant: BOSTON SCIENTIFIC SCIMED, INC., Maple Grove, MN (US)

(72) Inventors: Gary Gilmartin, Foxford (IE); Geraldine Toner, Raphoe (IE)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 247 days.

This patent is subject to a terminal disclaimer.

(21) Appl. No.: 18/321,441

(22) Filed: May 22, 2023

(65) Prior Publication Data

US 2023/0301809 A1 Sep. 28, 2023

Related U.S. Application Data

(63) Continuation of application No. 16/789,833, filed on Feb. 13, 2020, now Pat. No. 11,690,743.

(Continued)

(51) Int. Cl.
*A61F 2/966* (2013.01)
*A61F 2/848* (2013.01)

(52) U.S. Cl.
CPC .............. *A61F 2/966* (2013.01); *A61F 2/848* (2013.01)

(58) Field of Classification Search
CPC ........ A61F 2/2427; A61F 2/2436; A61F 2/95; A61F 2/962; A61F 2/966; A61F 2002/9665
See application file for complete search history.

(56) References Cited

U.S. PATENT DOCUMENTS 5,201,757 A 4/1993 Heyn et al.
5,238,004 A 8/1993 Sahatjian et al.
(Continued)

FOREIGN PATENT DOCUMENTS

CN 102159157 A 8/2011
CN 105283154 A 1/2016
(Continued)

OTHER PUBLICATIONS

International Search Report and Written Opinion date May 15, 2020 for International Application No. PCT/US2020/018060.

*Primary Examiner* — Diane D Yabut
*Assistant Examiner* — Christian D Knauss
(74) *Attorney, Agent, or Firm* — Seager, Tufte & Wickhem, LLP

(57) ABSTRACT

An example stent delivery system is disclosed. The example stent delivery system includes an outer shaft having a distal end region, an inner surface and a lumen extending therein. The delivery system also includes an inner shaft extending within the outer shaft lumen, the inner shaft having a stent receiving region disposed along a distal end region thereof. Additionally, the delivery system includes a stent disposed along the stent receiving region and a braided member positioned radially outward from an outer surface of the stent and radially inward from the inner surface of the outer shaft, the braided member being attached to an outer surface of the inner member proximal of the stent. Additionally, the delivery system includes a plurality of tether members coupled to the braided member, wherein longitudinal retraction of the outer shaft relative to the inner shaft exposes the stent from the braided member.

17 Claims, 14 Drawing Sheets

Related U.S. Application Data

(60) Provisional application No. 62/806,580, filed on Feb. 15, 2019.

(56) References Cited

U.S. PATENT DOCUMENTS 5,662,703 A 9/1997 Yurek et al.
5,690,644 A 11/1997 Yurek et al.
5,749,921 A 5/1998 Lenker et al.
5,772,609 A 6/1998 Nguyen et al.
5,824,041 A 10/1998 Lenker et al.
6,004,328 A * 12/1999 Solar ........................ A61F 2/958 623/1.11
6,059,813 A 5/2000 Vrba et al.
6,139,510 A 10/2000 Palermo
6,238,410 B1 5/2001 Vrba et al.
6,380,457 B1 4/2002 Yurek et al.
6,508,803 B1 1/2003 Horikawa et al.
6,544,278 B1 4/2003 Vrba et al.
6,702,843 B1 * 3/2004 Brown .................... A61F 2/958 623/1.11
6,755,855 B2 6/2004 Yurek et al.
6,942,682 B2 9/2005 Vrba et al.
6,945,990 B2 9/2005 Greenan
7,285,130 B2 10/2007 Austin
7,338,518 B2 3/2008 Chobotov
7,393,358 B2 7/2008 Malewicz
7,632,296 B2 12/2009 Malewicz
7,785,360 B2 8/2010 Freitag
7,794,488 B2 9/2010 Vrba et al.
7,918,880 B2 4/2011 Austin
7,955,370 B2 6/2011 Gunderson
8,016,872 B2 9/2011 Parker
8,048,139 B2 11/2011 Frid et al.
8,066,754 B2 11/2011 Malewicz
8,109,983 B2 2/2012 Gunderson et al.
8,372,133 B2 2/2013 Douk et al.
8,377,109 B2 2/2013 Vrba et al.
8,535,368 B2 9/2013 Headley, Jr. et al.
8,920,481 B2 12/2014 Stiger
8,968,381 B2 3/2015 Parker et al.
9,161,853 B2 10/2015 Dorn
9,265,639 B2 2/2016 Schneider et al.
9,622,895 B2 4/2017 Cohen et al.
9,687,369 B2 6/2017 Dorn et al.
9,717,612 B2 8/2017 Dorn et al.
9,724,216 B2 8/2017 Dorn et al.
9,801,745 B2 10/2017 Wubbeling et al.
9,820,878 B2 11/2017 Parker, Jr. et al.
9,913,742 B2 3/2018 Leanna et al.
9,931,232 B2 4/2018 Gunderson et al.
9,943,429 B2 4/2018 Headley, Jr. et al.
10,076,434 B2 9/2018 Frid et al.
2003/0040789 A1 2/2003 Colgan et al.
2003/0083730 A1 5/2003 Stinson
2003/0114910 A1 6/2003 Juhani et al.
2005/0240254 A1* 10/2005 Austin ...................... A61F 2/95 623/1.11
2006/0015135 A1 1/2006 Vrba et al.
2006/0030923 A1 2/2006 Gunderson
2006/0041302 A1 2/2006 Malewicz
2006/0085022 A1* 4/2006 Hayes ..................... A61F 2/958 606/192
2007/0208350 A1* 9/2007 Gunderson ............. A61F 2/966 623/1.11
2008/0027528 A1* 1/2008 Jagger ....................... A61F 2/95 623/1.11
2010/0069852 A1 3/2010 Kelley
2010/0331955 A1 12/2010 Vrba et al.
2011/0009943 A1* 1/2011 Paul ................ A61B 17/12131 623/2.11
2011/0034987 A1 2/2011 Kennedy
2011/0082464 A1 4/2011 Douk et al.
2011/0118817 A1 5/2011 Gunderson et al.
2011/0137396 A1 6/2011 Dorn et al.
2011/0152760 A1* 6/2011 Parker ............... A61M 25/1006 623/1.11
2012/0101562 A1* 4/2012 Gunderson ............. A61F 2/966 623/1.12
2013/0204345 A1* 8/2013 Cully ...................... A61F 2/966 29/446
2015/0250630 A1 9/2015 Irwin et al.
2016/0038322 A1 2/2016 Dorn
2016/0113795 A1 4/2016 Frid et al.
2016/0135973 A1 5/2016 Christakis et al.
2017/0135834 A1 5/2017 Tassoni, Jr. et al.

FOREIGN PATENT DOCUMENTS

EP 2813195 A1 12/2014
WO 0041525 A2 7/2000
WO 2006088638 A1 8/2006
WO 2010033698 A1 3/2010
WO 2014198941 A1 12/2014

* cited by examiner

STENT DELIVERY SYSTEM

CROSS-REFERENCE TO RELATED APPLICATIONS

This application is a continuation of U.S. application Ser. No. 16/789,833, filed Feb. 13, 2020, which claims the benefit of priority of U.S. Provisional Application No. 62/806,580 filed Feb. 15, 2019, the entire disclosures of which are hereby incorporated by reference.

TECHNICAL FIELD

The present disclosure pertains to medical devices and methods for making and using medical devices. More particularly, the present disclosure pertains to stent delivery systems.

BACKGROUND

A wide variety of intracorporeal medical devices have been developed for medical use, for example, intravascular use. Some of these devices include stent delivery systems. In some instances, an implantable medical device (e.g., self-expanding stents) may be used for treatment of the esophagus, a stenosis in a blood vessel, used to maintain a fluid opening or pathway in the vascular, urinary, biliary, tracheobronchial, esophageal, or renal tracts, or position a device such as an artificial valve or filter within a body lumen, for example.

Stents are generally tubular shaped devices which function to expand within a segment of a body lumen, such as an esophagus, a trachea, a colon, a blood vessel, or other body lumen or cavity. Stents are usually delivered in a compressed condition to a target site and then deployed at that location into an expanded condition to support the body lumen. During delivery, self-expanding stents are generally compressed, or otherwise radially constrained, to a reduced diameter that is smaller than its diameter when deployed at the target site. When positioned at the desired target site within the body lumen, the stent may be deployed by removing the constraining force, which allows the stent to self-expand to a diameter sufficient to treat the target tissue site.

In some instances, the constraining force placed upon the self-expanding stent may be imparted by an outer sheath or deployment tube. Retraction of the outer deployment tube relative to the self-expanding stent may release the stent from a compressed configuration to an expanded (e.g., deployed) configuration. However, in some instances, the inner surface of the deployment tube may impart undesirable frictional forces on the outer surface of the stent. These frictional forces may result in difficulty loading the stent into the deployment system and/or deploying the stent from the deployment system. Accordingly, it may be desirable to provide stent delivery systems designed to reduce the frictional forces between the outer deployment tube and the self-expanding stent.

BRIEF SUMMARY

This disclosure provides design, material, manufacturing methods, and use alternatives for medical devices. An example stent delivery system includes an outer shaft having a distal end region and an inner surface defining a lumen extending therein. The delivery system also includes an inner shaft extending at least partially within the lumen of the outer shaft, the inner shaft having a stent receiving region disposed along a distal end region thereof. Additionally, the delivery system includes a stent disposed along the stent receiving region, the stent having an outer surface. Further, the delivery system includes a braided member positioned radially outward from the outer surface of the stent and radially inward from the inner surface of the outer shaft, the braided member being attached to an outer surface of the inner member proximal of the stent. Additionally, the delivery system includes a plurality of tether members coupled to the braided member and extending therefrom, wherein longitudinal retraction of the outer shaft relative to the inner shaft exposes the stent from the braided member.

Alternatively or additionally to any of the embodiments above, wherein each of the plurality of tether members includes a first end directly attached to the braided member and a second end directly attached to the outer shaft.

Alternatively or additionally to any of the embodiments above, wherein the braided member includes a proximal end and a distal end, and wherein the proximal end of the braided member is attached to the outer surface of the inner member, and wherein the distal end is attached to the first end of each of the plurality of tether members.

Alternatively or additionally to any of the embodiments above, wherein the braided member is configured to space the inner surface of the outer shaft radially away from the outer surface of the stent.

Alternatively or additionally to any of the embodiments above, wherein the braided member exerts a radially compressive force along the stent.

Alternatively or additionally to any of the embodiments above, wherein retracting the outer shaft slides the inner surface of the outer shaft along an outer surface of the braided member.

Alternatively or additionally to any of the embodiments above, wherein the braided member includes a proximal end region, and wherein the proximal end region includes a tapered portion tapering to a smaller diameter in a proximal direction.

Alternatively or additionally to any of the embodiments above, wherein the braided member includes a longitudinal axis and a length measured along the longitudinal axis from a proximal end of the braided member to a distal end of the braided member, and wherein the braided member is configured to axially compress along the longitudinal axis as the outer member is retracted in a proximal direction such that the length of the braided member is reduced.

Alternatively or additionally to any of the embodiments above, wherein retraction of the outer shaft uncovers at least a portion of the braided member, and wherein the uncovered portion of the braided member expands radially outward as the outer member is retracted.

Alternatively or additionally to any of the embodiments above, wherein retraction of the outer shaft retracts the plurality of tether members in a proximal direction, and wherein retraction of the tether members folds the braided member back on itself.

Alternatively or additionally to any of the embodiments above, wherein the braided member includes a longitudinal axis, and wherein retraction of the outer shaft retracts the plurality of tether members, and wherein retraction of the plurality of tether members axially compresses the braided member along the longitudinal axis.

Alternatively or additionally to any of the embodiments above, wherein each of the plurality of tether members includes a first end attached to an outer surface of the inner shaft and a second end attached to a distal end of the braided member.

Alternatively or additionally to any of the embodiments above, wherein the outer shaft includes a plurality of apertures extending through a wall thickness of the outer member, and wherein each of the plurality of tether members passes through one of the plurality of apertures extending through the wall thickness of the outer member.

Alternatively or additionally to any of the embodiments above, wherein retraction of the outer shaft draws a portion of each of the plurality of tether members into the lumen of the outer shaft.

Another example stent delivery system includes an outer shaft having a distal end region, an inner surface and a lumen extending therein. The delivery system also includes an inner shaft extending at least partially within the lumen of the outer shaft, the inner shaft having a stent receiving region disposed along a distal end region thereof, wherein the inner shaft is designed to translate longitudinally relative to the outer shaft. Additionally, the delivery system includes a stent disposed along the stent receiving region, the stent having an outer surface, wherein the stent is configured to shift from a first radially collapsed configuration when subjected to a radially constraining force to a radially expanded configuration when free of the radially constraining force. The delivery system also includes a braided sleeve positioned between the outer surface of the stent and the inner surface of the outer shaft, the braided sleeve configured to radially compress the stent in the first configuration. Additionally, the delivery system includes one or more tether members coupled to the braided sleeve and extending therefrom, wherein longitudinal retraction of the outer shaft relative to the inner shaft exposes the stent from the braided member.

Alternatively or additionally to any of the embodiments above, wherein the braided member is configured to space the inner surface of the outer shaft radially away from the outer surface of the stent.

Alternatively or additionally to any of the embodiments above, wherein retracting the outer shaft slides the inner surface of the outer shaft along an outer surface of the braided sleeve.

Alternatively or additionally to any of the embodiments above, wherein each of the one or more tether members includes a first end directly attached to a distal end of the braided sleeve and a second end directly attached to the outer shaft.

Alternatively or additionally to any of the embodiments above, wherein each of the one or more tether members includes a first end attached to the inner member at a location proximal of the stent and a second end attached to a distal end of the braided sleeve.

An examples method of treating a body lumen includes advancing a stent delivery system to a target tissue site, wherein the stent delivery system includes an outer shaft having a distal end region and an inner surface defining a lumen extending therein, an inner shaft extending at least partially within the lumen of the outer shaft, the inner shaft having a stent receiving region disposed along a distal end region thereof, a stent disposed along the stent receiving region, the stent having an outer surface, a braided sleeve positioned radially outward from the outer surface of the stent and radially inward from the inner surface of the outer shaft, the braided sleeve being attached to an outer surface of the inner member proximal of the stent, and one or more tether members, a first end of each of the one or more tether members being coupled to a distal end of the braided sleeve and extending therefrom. The method further includes retracting the outer shaft relative to the inner shaft to apply a tension force to the one or more tether members to proximally retract the distal end of the braided sleeve to expose the stent from the braided sleeve and permit the stent to radially expand.

The above summary of some embodiments is not intended to describe each disclosed embodiment or every implementation of the present disclosure. The Figures, and Detailed Description, which follow, more particularly exemplify these embodiments.

BRIEF DESCRIPTION OF DRAWINGS

The disclosure may be more completely understood in consideration of the following detailed description of various embodiments of the disclosure in connection with the accompanying drawings, in which.

Figure 1:
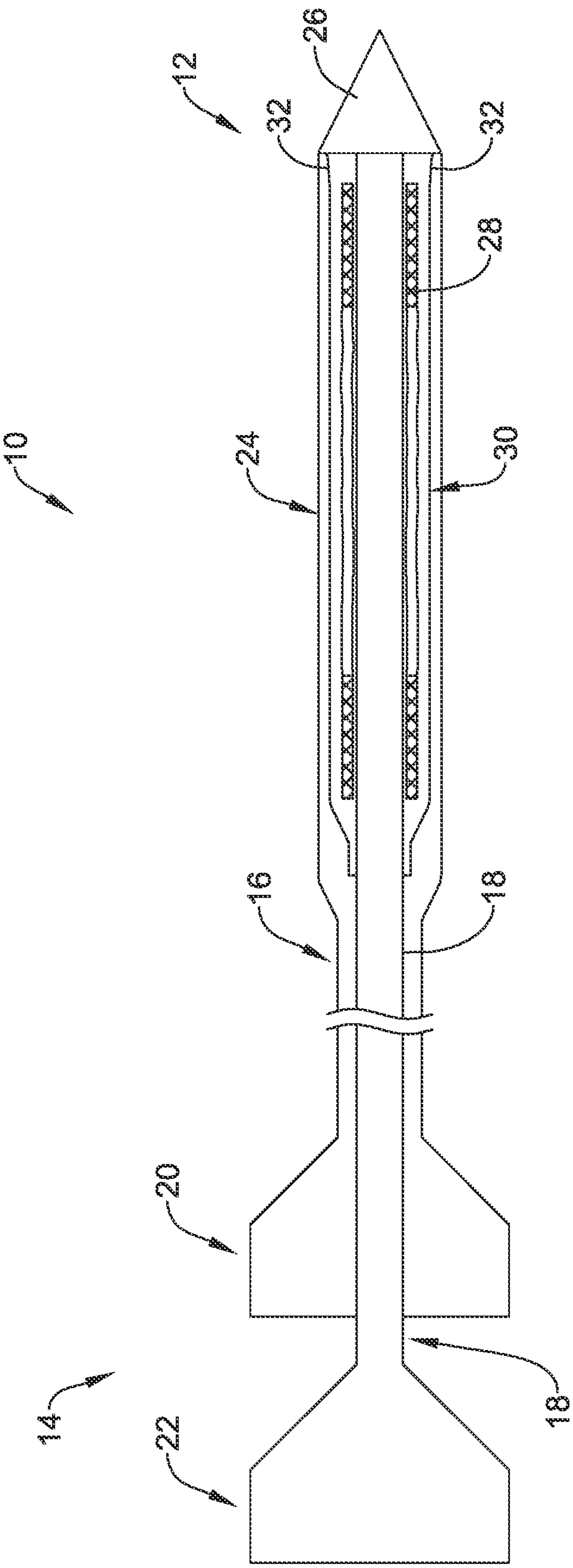
FIG. 1 illustrates a side view of an example stent delivery system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term “about,” whether or not explicitly indicated. The term “about” generally refers to a range of numbers that one of skill in the art would consider equivalent to the recited value (i.e., having the same function or result). In many instances, the terms “about” may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms “a”, “an”, and “the” include plural referents unless the content clearly dictates otherwise. As used in this specification and the appended claims, the term “or” is generally employed in its sense including “and/or” unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the disclosure.

FIG. 1 illustrates an example medical device delivery system 10, such as a stent delivery system. In general, the system 10 may be configured to position an implantable medical device (e.g., a stent 28) in a body lumen for a variety of medical applications. For example, the stent 28 may be used to treat a stenosis in a blood vessel, used to maintain a fluid opening or pathway in the vascular, urinary, biliary, tracheobronchial, esophageal, or renal tracts, or position a device such as an artificial valve or filter within a body lumen, in some instances. In some instances, the stent 28 may include a prosthetic graft, a stent-graft, or a stent (e.g., a vascular stent, tracheal stent, bronchial stent, esophageal stent, etc.), an aortic valve, filter, etc. Although illustrated as a stent, the stent 28 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

As stated above, during delivery, self-expanding stents are generally compressed, or otherwise radially constrained, to a reduced diameter that is smaller than its diameter when deployed at the target site. When positioned at the desired target site within the body lumen, the stent may be deployed by removing the constraining force, which allows the stent to self-expand to a diameter sufficient to treat the target tissue site.

Further, as discussed above, in some examples the radially constraining force placed upon the self-expanding stent may be imparted by an outer deployment sheath. Retraction of the outer deployment sheath relative to the self-expanding stent may release the stent from a compressed (e.g., loaded) configuration to a radially expanded (e.g., deployed) configuration. However, in some instances, the inner surface of the deployment tube may impart undesirable frictional forces on the outer surface of the stent. These frictional forces may result in difficulty loading the stent into the deployment system and/or deploying the stent from the deployment system. Examples disclosed herein provide stent delivery systems designed to reduce the frictional forces between the outer deployment tube and the self-expanding stent.

The example stent delivery system 10 illustrated in FIG. 1 may include a distal end region 12 and a proximal end region 14. Further, the system 10 may include an outer sheath 16. The outer sheath 16 may include a distal end region 24 and a proximal end coupled to a handle 20. The outer sheath 16 may include a lumen extending therein. Further, the delivery system 10 may include an inner member 18, such as an inner tubular member, extending at least partially within the lumen of the outer sheath 16. In some instances, the inner tubular member 18 may extend along the entire length of the lumen of the outer sheath 16. The inner tubular member 18 may be longitudinally translatable or movable relative to the outer sheath 16.

The inner tubular member 18 may include a proximal end which is coupled to a handle 22 and a distal end which includes or is coupled to a tip 26. The tip 26 may be attached to, incorporated with, or otherwise disposed at the distal end of inner member 18. The tip 26 may generally have a tapered, rounded or smooth shape that provides a generally atraumatic distal end to system 10. For example, the tip 26 may have a smooth distal portion that gently tapers in a proximal-to-distal direction. In some examples a portion of the inner member 18 may extend into a portion of the tip 26 and be secured thereto. However, in other examples it is contemplated that the tip 26 and the inner member 18 may be formed as a monolithic structure. Additionally, while not shown in FIG. 1 for simplicity purposes, it can be appreciated that the inner member 18 may include a lumen extending therein, in some instances. The lumen of the inner member 18 may be designed to accommodate a guidewire extending therein.

The inner member 18 may include a stent receiving region about which a stent 28 may be disposed. The length and/or configuration of the stent receiving region may vary. For example, the stent receiving region may have a length sufficient for the stent 28 to be disposed thereon in a radially compressed, constrained configuration within outer sheath 16. In other words, the stent 28 may surround the stent receiving region of the inner member 18 with the stent 28 positioned in a compressed (e.g., loaded) configuration between the inner surface of the outer sheath 16 (e.g., the inner surface which defines the lumen of the outer sheath 16) and the outer surface of the inner member 18. In other words, the distal end region 24 of the outer sheath 16 may compress the stent 28 radially inward along the outer surface of the inner member 18. It can be appreciated that the length of the stent 28 utilized for system 10 may dictate the desired length of the stent receiving region to accommodate stent 28.

However, FIG. 1 further illustrates that, in some examples, the stent delivery system may further include a friction-reducing member 30 (e.g., a friction-reducing sleeve) surrounding the stent 28 and positioned between the outer surface of the stent 28 and the inner surface of the distal end region 24 of the outer sheath 16. In other words, the friction-reducing member 30 may be positioned radially outward of the outer surface of the stent 28 and radially inward of the inner surface of the outer sheath 16 to space the stent away from direct contact with the inner surface of the outer sheath 16. The friction-reducing member 30 may be designed to reduce the frictional forces exerted on the outer surface of the stent 28 during both deployment of the stent 28 and/or loading of the stent 28 into the stent delivery system 10.

As will be discussed in greater detail below, the friction-reducing member 30 may include a proximal end which is secured to the inner member 18 proximal of the proximal end of the stent 28. For example, the proximal end of the friction-reducing member 30 may be affixed to the outer surface of the inner member 18 at a location proximal of the stent receiving region, and thus proximal of the stent 28. The friction-reducing member 30 may extend over the entire length of the constrained stent 28, with a distal end of the friction-reducing member 30 located distal of the distal end of the stent 28 in the radially contracted configuration when loaded within the outer sheath 16. The proximal end of the friction-reducing member 30 may be the only portion of the friction-reducing member 30 directly secured to the inner member 18, with the remainder of the length of the friction-reducing member 30 surrounding, but spaced away from the inner member 18.

Additionally, the friction-reducing member 30 may include a distal end coupled to one or more, or a plurality of tether members 32. The tether members 32 may have a first end which is coupled to (e.g., tied to) the distal end of the inner tubular member 18 (as discussed). In some instances, a second end (opposite the first end) of the tether members 32 are coupled to the outer sheath 16 or otherwise engaged with the outer sheath 16. In other instances, the second end of the tether members 32 may be coupled to the inner member 18 at a location proximal of the stent 28. Further discussion of the friction-reducing member 30 is presented below.

Deployment of the stent 28 at a target tissue site may include retracting the outer sheath 16 relative to the inner member 18 to uncover the stent 28 from the outer sheath 16 (which is disposed over the stent 28 during delivery). For example, the outer sheath 16, which may overlie the stent 28, may be proximally retracted (relative to the stent 28) in a distal-to-proximal direction such that the stent 28 is uncovered. In other instances, distal advancement of the outer sheath 16 (relative to the stent 28) may cover the stent 28 when being positioned in a loaded configuration within the stent delivery system 10. Longitudinal actuation (proximal retraction and/or distal advancement) of the outer sheath 16 may include actuation (e.g., proximal retraction and/or distal advancement) of a handle member 20 coupled to the proximal end of the outer sheath 16 relative to a handle member 22 coupled to the proximal end of the inner member 18.

Figure 2:
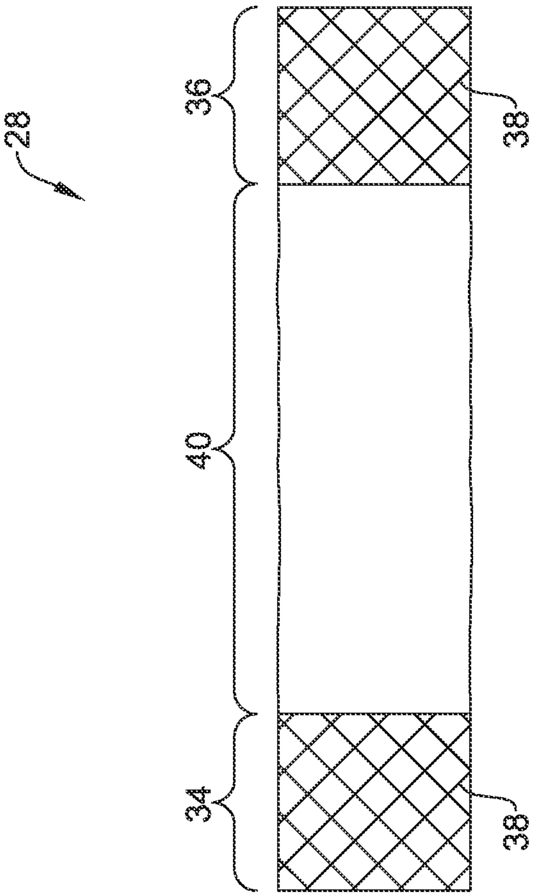
FIG. 2 illustrates an example self-expanding stent.

FIG. 2 illustrates one possible configuration of the example stent 28, although other stent configurations may be used with the stent delivery system 10, if desired. The stent 28 may have a first end region 34 and a second end region 36 positioned on an opposite end of the stent 28 from the first end region 34. In some instances, the first end region 34 may extend to a first end of the stent 28 and the second end region 36 may extend to a second end of the stent 28 opposite the first end. The first end region 34 may be attached to the second end region 36 via a medial region 40 to form an expandable tubular stent having open ends and defining a lumen extending therein. While not shown in FIG. 2, the first end region 34 and/or the second end region 36 may include a flared portion, if desired.

FIG. 2 illustrates that each of the first end region 34 and the second end region 36 of the stent 28 may include a plurality of strut members 38 arranged in a variety of different designs and/or geometric patterns to form the expandable first end region 34 and the second end region 36 of the stent 28. Numerous designs, patterns and/or configurations for the stent cell openings, strut thicknesses, strut designs, stent cell shapes are contemplated and may be utilized with embodiments disclosed herein. Further, self-expanding stent examples disclosed herein may include stents having one or more strut members 38 combined to form a rigid and/or semi-rigid stent structure. In some examples disclosed herein, the collection of strut members 38 forming the first end region 34 and/or the second end region 36 of the stent 28 may form a rigid and/or semi-rigid framework structure. For example, the strut members 38 may be wires or filaments braided, intertwined, interwoven, weaved, knitted, crocheted or the like to form the expandable first end region 34 and/or the second end region 36 of the stent 28. The strut members (e.g., wires or filaments) 38 of the stent 10 may be configured to self-expand to an expanded diameter when unconstrained. Alternatively, the strut members 38 may be formed from a monolithic structure (e.g., a cylindrical tubular member), such as a single, cylindrical tubular laser-cut Nitinol tubular member, in which the remaining portions of the tubular member form the strut members 38. The monolithic structure of the stent 10 may be configured to self-expand an expanded diameter when unconstrained.

The radially expandable first end region 34 and/or the second end region 36 of the stent 28 in at least some examples disclosed herein may be constructed from a variety of materials. For example, the expandable first end region 34 and/or the second end region 36 of the stent 28 may be constructed from a metal (e.g., Nitinol). In other instances, the expandable first end region 34 and/or the second end region 36 of the stent 28 may be constructed from a polymeric material (e.g., PET). In yet other instances, the expandable first end region 34 and/or the second end region 36 of the stent 28 may be constructed from a combination of metallic and polymeric materials. Additionally, the expandable first end region 34 and/or the second end region 36 of the stent 28 or portions thereof may include a bioabsorbable and/or biodegradable material.

In some instances, the example stent 28 may include one or more layers (e.g., covering, coating, etc.) of material positioned on and/or adjacent to the outer surface of the stent 28. For example, the first end region 34 and/or the second end region 36 of the stent 28 may include a covering of material positioned on and/or adjacent to the strut members 38. In some instances, the outer layer or covering may be an elastomeric or non-elastomeric material. For example, the outer layer or covering may be a polymeric material, such as silicone, polyurethane, or the like. Further, the outer layer may span the spaces (e.g., openings, cells, interstices) between strut members 38 of the first end region 34 and/or the second end region 36 of the stent 28.

In some examples, the medial region 40 stent 28 may include a flexible polymeric portion which has no underlying stent support. For example, the medial region 40 may include a tubular polymeric portion having an inner surface and an outer surface. The medial region 40 may include a first end which is coupled to the first end region 34 of the stent 28 and a second end which is coupled to the second end region 36 of the stent 28. Thus, the medial region 40 may consist only of the polymeric covering spanning between the first end region 34 and the second end region 36 of the stent 28.

Figure 3:
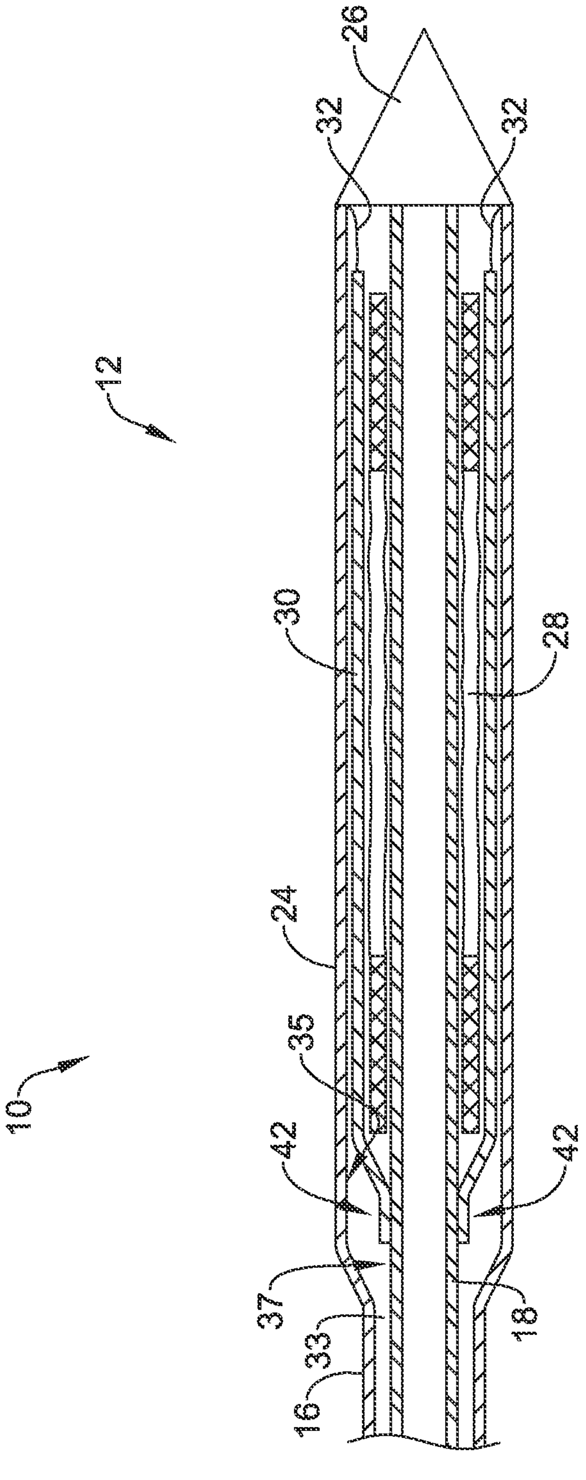
FIG. 3 illustrates a cross-sectional side view of a portion of the example stent delivery system shown in FIG. 1.

FIG. 3 illustrates the distal end region 12 of the stent 10 including a distal end region 24 of the outer sheath 16. Additionally, FIG. 3 shows the inner tubular member 18 positioned within the lumen 33 of the outer sheath 16. The distal end of the inner tubular member 18 is coupled to a tip 26. Additionally, FIG. 3 illustrates the friction-reducing member 30 positioned radially outward of the stent 28 and radially inward of the inner surface 35 of the distal end region 24 of the outer sheath 16, spacing the radially constrained stent 28 away from frictional contact with the inner surface 35 of the outer sheath 16. In some instances, the friction-reducing member 30 may be described as a sleeve covering or surrounding the stent 28 while in a compressed configuration. As discussed above, the proximal end of the friction-reducing member 30 may be coupled to the outer surface 37 of the inner tubular member 18 at an attachment point 42 proximal of the stent 28. Additionally, the distal end of the friction-reducing member 30 may extend distally beyond the stent 28 and be coupled to the outer sheath 16 via one or more, or a plurality of tether members 32.

Figure 4:
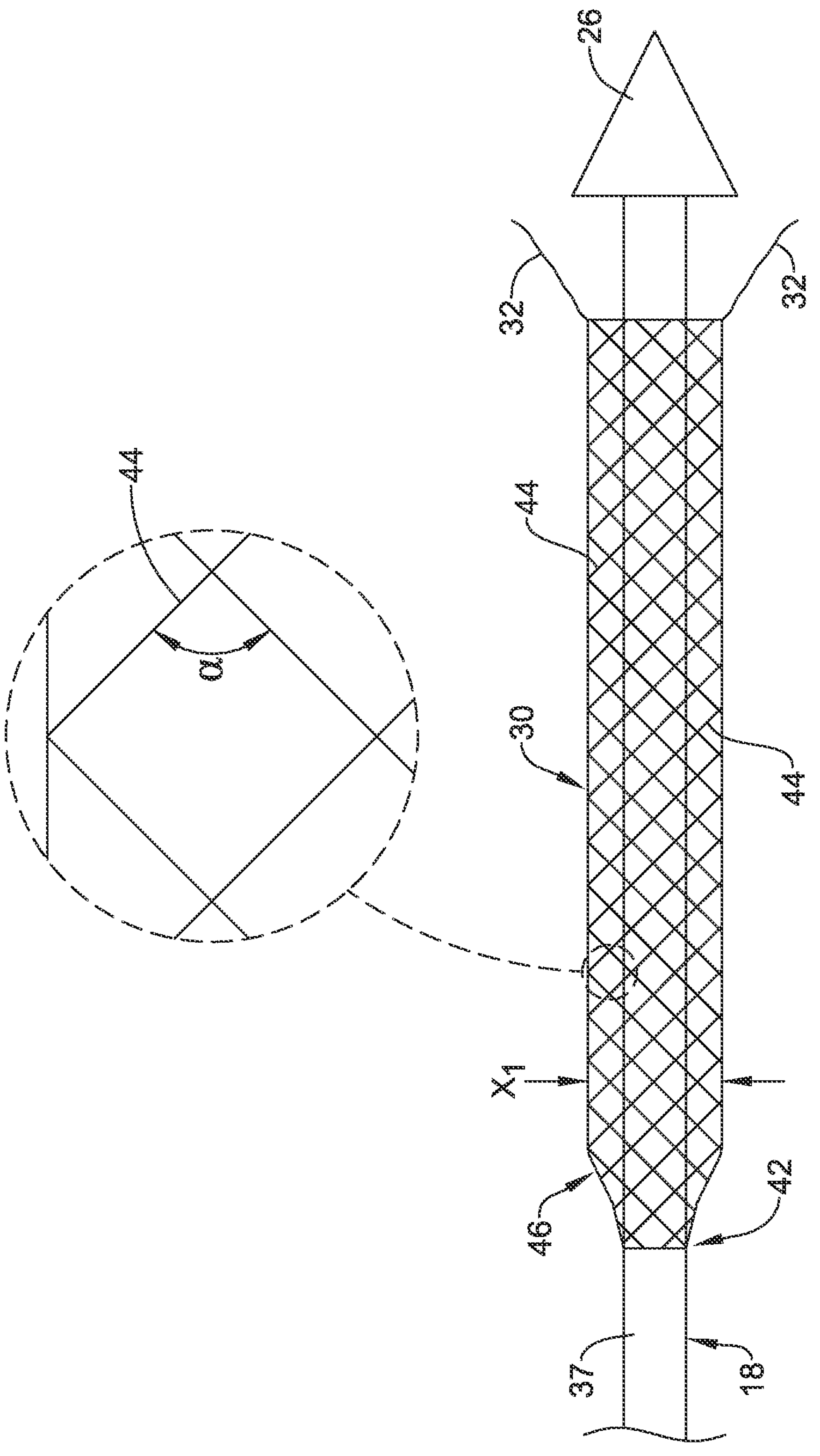
FIG. 4 illustrates a portion of the stent delivery system shown in FIG. 1.

FIG. 4 illustrates a portion of the stent delivery system 10 described above. In particular, FIG. 4 illustrates the friction-reducing member 30 secured to and disposed along the inner member 18. It is noted that to better illustrate the friction-reducing member 30 disposed along the inner member 18, the outer sheath 16 and the stent 28 have been omitted from FIG. 4. Additionally, FIG. 4 illustrates the friction-reducing member 30 in an unconstrained configuration. In other words, FIG. 4 illustrates the friction-reducing member 30 in its configuration when free of the outer sheath 16. The proximal end of the friction-reducing member 30 may be the only portion of the friction-reducing member 30 directly secured to the inner member 18, with the remainder of the length of the friction-reducing member 30 surrounding, but spaced away from the inner member 18.

In some examples, the friction-reducing member 30 shown in FIG. 4 may include a woven structure (e.g., a braided tubular member) formed from one or more, or a plurality of filaments 44 which are braided, intertwined, interwoven, weaved, knitted, crocheted or the like to form the tubular friction-reducing member 30. The detailed view of FIG. 4 illustrates that, when unconstrained, the filaments 44 of friction-reducing member 30 may intersect one another at a braid angle depicted as "a" in FIG. 4. Alternatively, the friction-reducing member 30 may be formed from a monolithic structure (e.g., a cylindrical tubular member), such as a single, cylindrical tubular laser-cut tubular member, in which the remaining portions of the tubular member form the friction-reducing member 30.

As shown in FIG. 4, the friction-reducing member 30 may be tubular and include a lumen through which at least a portion of the inner member 18 may extend. For example, FIG. 4 illustrates the inner member 18 extending through the entire length of the friction-reducing member 30 such that the distal tip 26 is located distal of the friction-reducing member 30. Additionally, FIG. 4 illustrates that the proximal end of the friction-reducing member 30 may be secured to the inner member 18, such as attached to the outer surface 37 of the inner member 18 at the attachment point 42. FIG. 4 further illustrates that, when unconstrained, the friction-reducing member 30 may include an outer diameter X1. Further, the friction-reducing member 30 may include a tapered portion 46 which tapers longitudinally (and radially outward) from the attachment point 42 to a position along the outer surface of the friction-reducing member 30 having the diameter X1. Additionally, FIG. 4 illustrates the tether members 32 attached to the distal end of the friction-reducing member 30 and extending therefrom.

The tether members 32 may include a variety of materials. For example, the tether members 32 may be formed from an inelastic or elastic material. In some instances, the tether members 32 may include a suture, a thread, a wire or any other similar structure.

Additionally, the friction-reducing member 30 (including filaments 44) may be constructed from a variety of materials. For example, the friction-reducing member 30 (including filaments 44) may be constructed from a metal (e.g., Nitinol). In other instances, the friction-reducing member 30 (including filaments 44) may be constructed from a polymeric material (e.g., PET, PTFE, PEEK, etc.). In yet other instances, the friction-reducing member 30 (including filaments 44) may be constructed from a combination of metallic and polymeric materials. Additionally, the friction-reducing member 30 (including filaments 44) or portions thereof may include a bioabsorbable and/or biodegradable material. In some instances, filaments 44 of the friction-reducing member 30 may be coated with polytetrafluoroethylene (PTFE) or other low friction material.

As will be further illustrated, in some instances it may be desirable to design the friction-reducing member 30 to change shape and/or manipulate the shape of the friction-reducing member 30 during deployment of the stent 28. For example, as the stent delivery system 10 is manipulated to deploy the stent 28, the friction-reducing member 30 may extend out of the distal end of the outer sheath 16 and eventually fold back on itself. In other words, as the outer sheath 16 is retracted (relative to the stent 28 as described above) to uncover and deploy the stent 28, a portion (or all of) the friction-reducing member 30 may also be uncovered. Further, because the distal end of the friction-reducing member 30 is coupled to the tether members 32, as the outer sheath 16 is retracted the friction reducing member 30 a tensile force applied to the tether members 32 may cause the distal end of the friction-reducing member 30 to be retracted proximally toward the proximal end of the friction reducing member 30.

Figure 5:
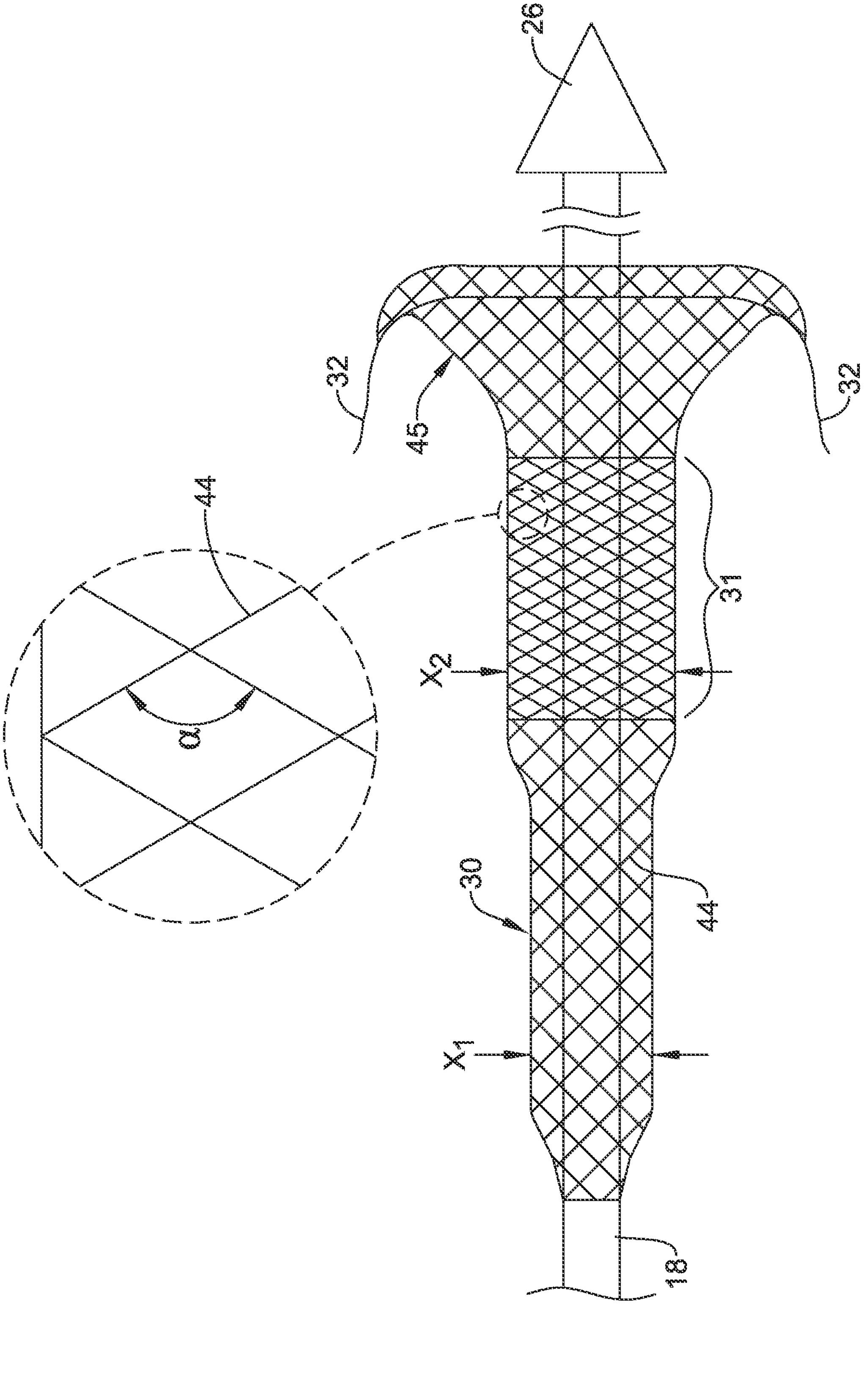
FIG. 5 illustrates a portion of the stent delivery system shown in FIG. 1.

FIG. 5 illustrates the friction-reducing member shown in FIG. 4 in an example "retracted" configuration. In other words, FIG. 5 illustrates an example configuration of the friction-reducing member 30 after having been partially retracted as the outer sheath 16 is retracted. Similar to FIG. 4, the outer sheath 16 and the stent 28 have be omitted from FIG. 5 for simplicity.

FIG. 5 shows that as the outer sheath 16 is retracted, the tether members 32 may pull on the distal end of the friction-reducing member 30. Consequently, in some examples, the distal end of the friction-reducing member 30 may fold back on itself, as illustrated in FIG. 5. Additionally, FIG. 5 illustrates that as the friction-reducing member 30 folds back on itself, it may also collapse along its longitudinal axis (e.g., it may "accordion" along its longitudinal axis). FIG. 5 identifies the collapsed region of the friction-reducing member 30 by reference numeral 31. Additionally, the detailed view of FIG. 5 illustrates that the angle "a" (defined as the braid angle between filaments 44 as described in FIG. 4) may increase as the filaments 44 accordion with respect to one another.

As can be seen from FIG. 5, as the friction-reducing member 30 is uncovered from the outer sheath 16 (e.g., by withdrawing the outer sheath 16 proximally relative to the friction-reducing member 30), forces applied to the friction-reducing member 30 by the tethers 32 may retract the distal end of the friction-reducing member 30 toward its proximal end, and thus its shape may change from its equilibrium or unconstrained shape as shown in FIG. 4. For example, at least a portion of the length of the friction-reducing member 30 may be longitudinally collapsed, and thus reduced in axial length from its unconstrained length. For example, FIG. 5 illustrates that the outer diameter X2 of the longitudinally collapsed region 31 may be greater than the outer diameter X1 described in FIG. 5. In other words, as the distal end of the friction-reducing member 30 is retracted proximally, it may both collapse along the longitudinal axis and also expand radially outward. Further, FIG. 5 illustrates that as the friction-reducing member 30 is retracted, the distal end region may include a flared region 45 in some instances.

Figure 6:
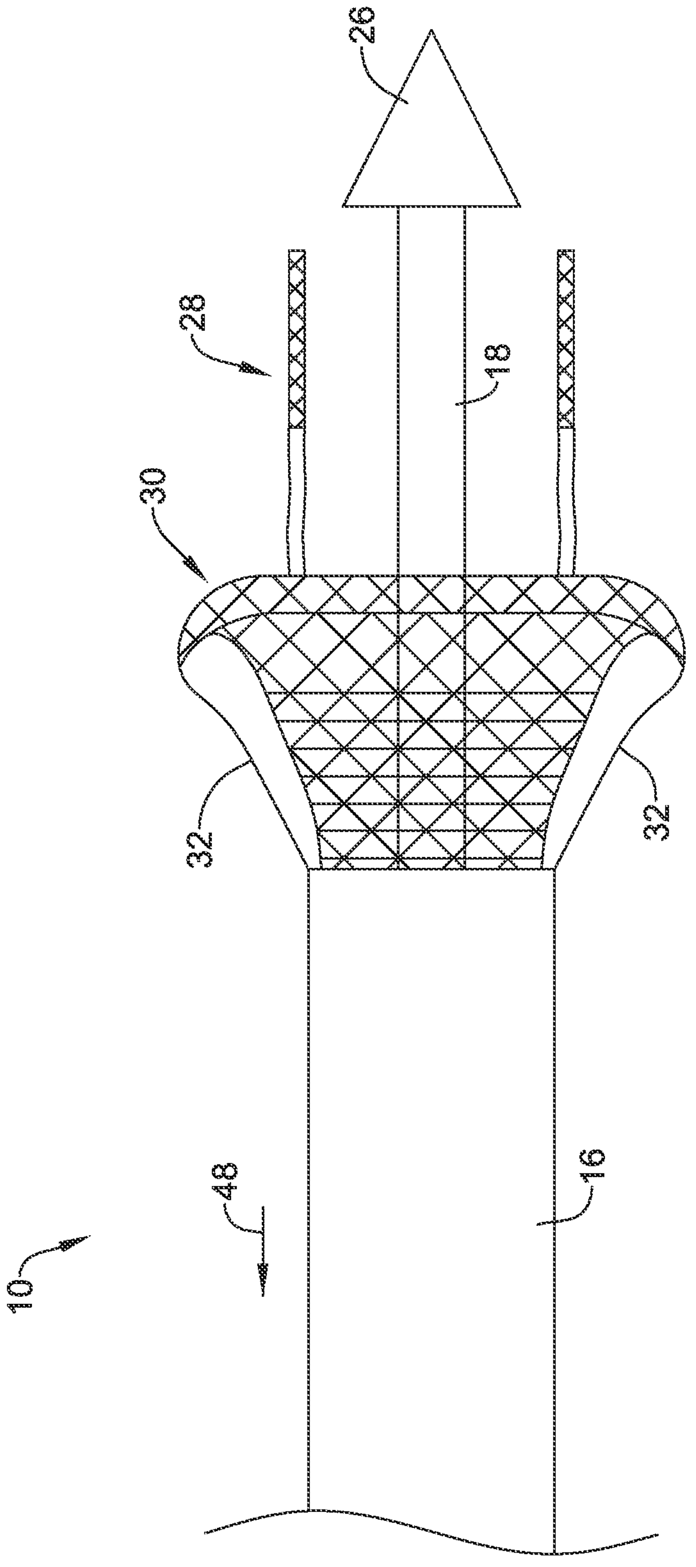
FIG. 6 illustrates the example stent delivery system of FIG. 1 during a stage of deployment of a stent.
Figure 7:
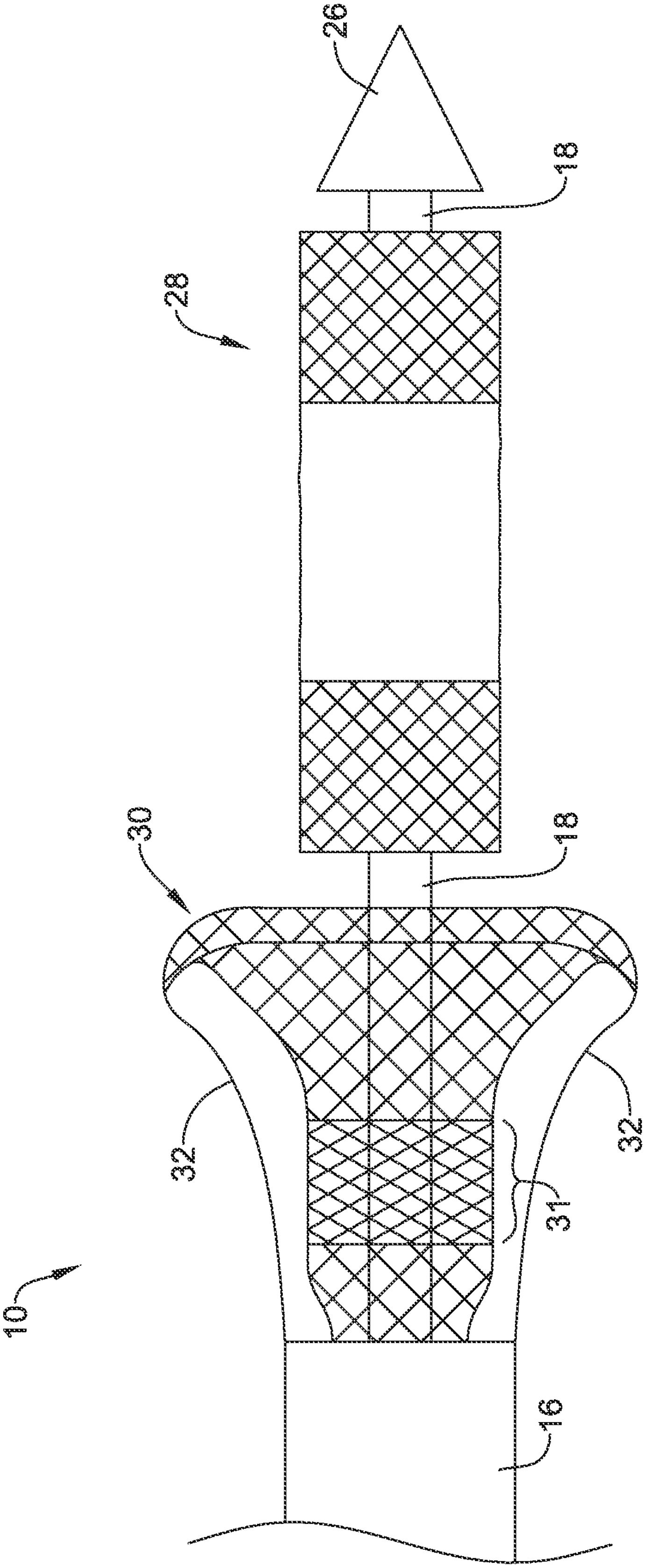
FIG. 7 illustrates the example stent delivery system of FIG. 1 during another stage of deployment of a stent.

FIG. 6 and FIG. 7 illustrate a sequence of steps showing the deployment of the stent 28 from the stent delivery system 10. As illustrated in FIG. 1, the system 10 may include an inner tubular member 18. In at least some embodiments, the inner member 18 may be attached to a handle member 22 positioned along a proximal portion thereof.

As discussed above, the stent 28 may be disposed about (i.e., surround) the inner member 18 (e.g., surround the stent receiving region of inner member 18). In some embodiments, the stent 28 may be a self-expanding stent, with the stent 28 held in a radially constrained configuration during delivery to a deployment location of a patient. Accordingly, the stent 28 may be biased to outwardly expand when unconstrained and deployed from the stent delivery system 10. For example, the stent 28 may be loaded onto the inner member 18 by radially compressing the stent 28 around the inner member 18. The stent 28 may then be restrained within the outer sheath 16 in the radially compressed configuration as the outer sheath 16 surrounds the stent 28 in the radially compressed configuration. In alternative embodiments, however, the stent 28 may be directly loaded onto the inner member 18 via crimping or any other suitable mechanical holding mechanism.

FIG. 6 illustrates the outer sheath 16 after being proximally retracted (as indicated by the arrow 48) to partially uncover the stent 28. It can be appreciated that FIG. 6 and FIG. 7 illustrate the outer sheath 16 shifting from a first position where the outer sheath 16 and the friction-reducing member 30 overlie the stent 28 to a second position where the outer sheath 16 is withdrawn proximal of the stent 28 such that the stent 28 is free from the outer sheath 16 and the friction-reducing member 30.

FIG. 6 illustrates an example step in the deployment of the stent 28. It can be appreciated that prior to the deployment step illustrated in FIG. 6, the system 10 may have been navigated to a position adjacent to a target site in a body lumen. Once navigated to a desired location, a clinician or other operator may retract the outer sheath 16 relative to the inner member 18 and the stent 28. As stated above, the stent 28 may be a self-expanding stent biased to expand radially outward when unconstrained. Therefore, it can be appreciated that as the outer sheath 16 is retracted in a proximal direction (thereby exposing a portion of the stent 28), the exposed portion of the stent 28 may automatically radially expand outward. FIG. 6 illustrates an exposed portion of the stent 28 expanding radially away from the inner member 18 as the outer sheath 16 is translated in a proximal direction (as depicted by the proximal pointing arrow 48).

As discussed above, FIG. 6 further illustrates that as the outer sheath 16 is retracted proximal, a portion of the friction-reducing member 30 may be exposed from the distal opening of the lumen of the outer sheath 16 and extend in a distal direction out of the distal end of the outer sheath 16. However, because the tether members 32 are attached to both the distal end of the outer sheath 16 and the distal end of the friction-reducing member 30, continued proximal retraction of the outer sheath 16 may pull the distal end of the friction-reducing member 30 in a proximal direction once the tethers 32 have been pulled taut and a tensile force exerted on the tethers through proximal retraction of the outer sheath 16. As discussed with respect to FIG. 5, as the friction-reducing member 30 emerges from the distal end region 24 of the outer sheath 16, the distal end region of the friction-reducing member 30 may initially flare radially outward in addition to folding back on itself (as shown in FIG. 6).

FIG. 7 illustrates the stent 28 after the outer sheath 16 has been retracted proximally to a position in which the distal end of the outer sheath 16 is proximal of the proximal end of the stent 28 and the stent 28 is free from both the outer sheath 16 and the friction-reducing member 30. As shown in FIG. 7, proximal retraction of the outer sheath 16 may draw the distal end of the friction-reducing member 30 to a position proximal of the stent 28 to fully expose and release the stent 28 during deployment. As discussed above, FIG. 7 illustrates that retraction of the outer sheath 16 to fully uncover the stent 28 may result in the friction-reducing member 30 longitudinally collapsing along a portion thereof (the collapsed region being identified by reference numeral 31 in FIG. 7). Thus, a longitudinal region of the friction-reducing member 30 may axially shorten during retraction of the outer sheath 16.

It can be appreciated that the friction-reducing member 30 may be designed to reduce the frictional forces generated along the inner surface of the outer sheath 16 as the outer sheath 16 is proximally retracted (to deploy the stent 28, as discussed above) as the frictional forces are generated between the inner surface of the outer sheath 16 and the friction-reducing member 30, instead of between the inner surface of the outer sheath 16 and the stent 28. It can further be appreciated that the braided configuration of the friction-reducing member 30 may reduce and/or limit the degree to which the inner surface of the outer sheath 16 contacts the friction-reducing member 30. Further, the specific material utilized to form the friction-reducing member 30 may help reduce the friction forces generated by the inner surface of the outer sheath 16. In some examples, the friction-reducing member 30 may be formed from a metal (e.g., Nitinol), a polymer, or a combination of metallic and polymeric materials.

Additionally, while the above discussion has focused on the ability of the friction-reducing member 30 to reduce or eliminate the friction forces generated between the outer sheath 16 and the stent 28 during deployment, it can be appreciated that the friction-reducing member 30 may also reduce or eliminate the friction forces generated between the outer sheath 16 and the stent 28 during loading of the stent 28. For example, when loading the stent 28, it can be appreciated that the stent delivery system 10 may be configured as shown in FIG. 7, whereby the stent 28 is compressed radially inward and funneled in a distal-to-proximal direction into the friction-reducing member 30. The braided structure of the friction-reducing member 30 may exert a radially inward force upon the stent 28 without appreciably exerting longitudinal frictional forces upon the stent 28, thereby helping to maintain the stent 28 in a radially compressed configuration as the outer sheath 16 is advanced in a proximal-to-distal direction over the friction-reducing member 30 and the stent 28. It can further be appreciated that as the outer sheath 16 is advanced in a proximal-to-distal direction, the outer sheath 16 may push, extend, or unroll the braided structure of the friction-reducing member 30 longitudinally along the outer surface of the stent 28 in a proximal-to-distal direction. Further, the flexibility of the braided structure of the friction-reducing member 30 may permit the friction-reducing member 30 to "swallow" the stent 28 (and thereby radially constrict the stent 28) within the friction-reducing member 30 as the outer sheath 16 is advanced in a proximal-to-distal direction relative to the stent 28.

Figure 8:
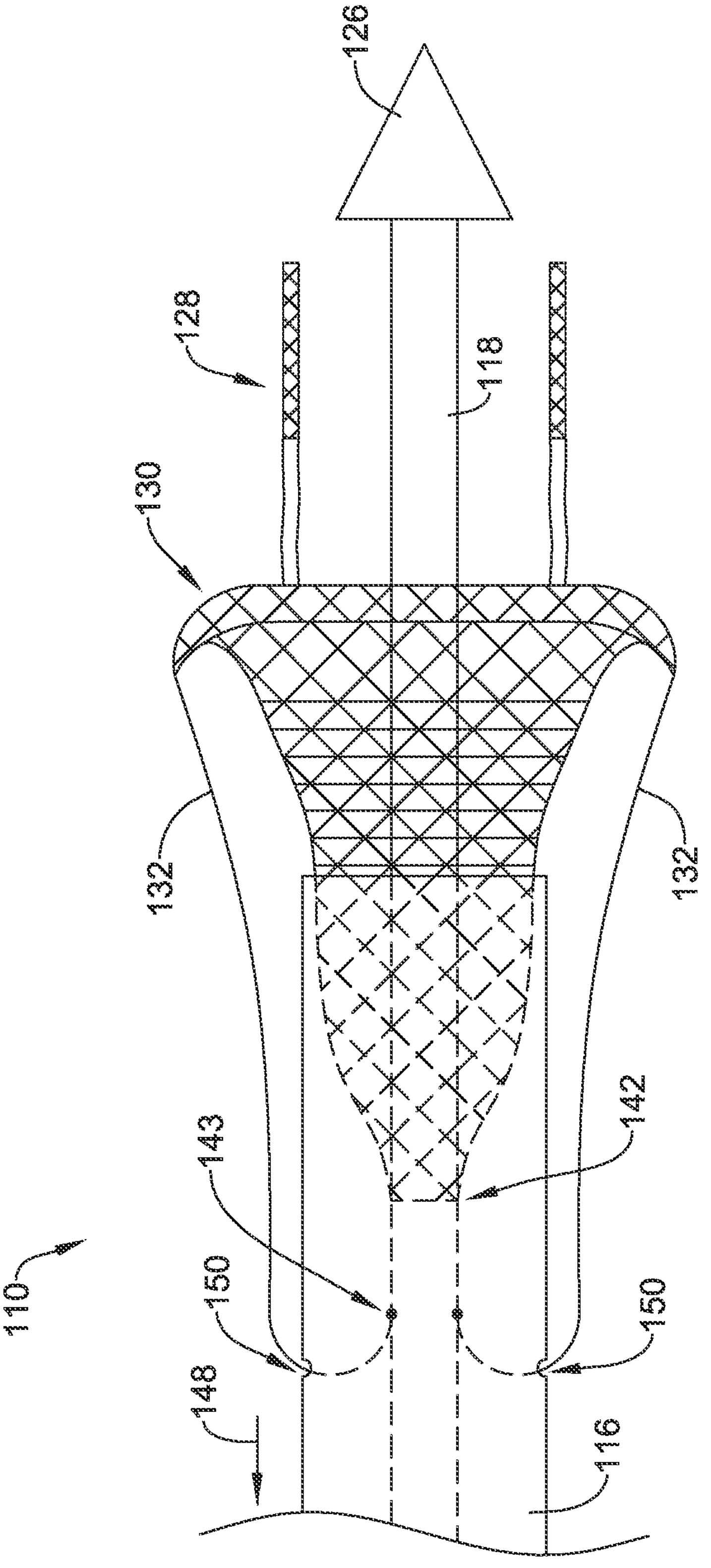
FIG. 8 illustrates a side view of another example stent delivery system.

FIG. 8 illustrates another example stent delivery system 110. The stent delivery system 110 may be similar in form and function to the stent delivery system 10 described above. For example, the stent delivery system 110 may include an inner member 118 extending through a lumen of an outer sheath 116 and longitudinally moveable relative to the outer sheath 116. In some instances, the inner member 118 may be a tubular member defining a guidewire lumen extending therethrough. The distal end of the inner member 118 may include or be attached to a distal tip member 126. Additionally, the stent delivery system 110 may include a friction-reducing member 130, such as a braided tubular sleeve. The proximal end of the friction-reducing member 130 may be secured to the inner member 118 at an attachment point 142. For example, the proximal end of the friction-reducing member 130 may be affixed to an outer surface of the inner member 118. Further, the stent delivery system 110 may include one or more, or a plurality of tether members 132, each having a first end attached to the distal end region of the friction-reducing member 130 and extending therefrom. The second, or opposite ends of the tether members 132 may be secured to the inner member 118 at an attachment point 143. The attachment point 143 may be located proximal of the proximal end of the friction-reducing member 130 and therefore proximal of the stent 128. Additionally, FIG. 8 illustrates that, in some examples, the tether members 132 may attach to the inner member 118 by passing through one or more apertures 150 (e.g., one or more "pin holes") extending through the wall of the outer sheath 116. Thus, the tethers 132 may extend from the distal end of the friction-reducing member 130 along an exterior of the outer sheath 116 and then pass through the wall of the outer sheath 116 through apertures 150 into the interior or lumen of the outer sheath 116 to be secured to the inner member 118. In some instances, the apertures 150 may be located proximal of the attachment point 143 when the outer sheath 116 is retracted proximally, thus the tethers 132 may extends proximally along the exterior of the outer sheath 116 to the apertures, and then extend distally from the apertures to the attachment point 143 through the lumen of the outer sheath 116.

FIG. 8 illustrates the stent delivery system 110 in a similar configuration as FIG. 6 described above. For example, FIG. 8 illustrates that as the outer sheath 116 is retracted proximally (as indicated by the arrow 148), a portion of the friction-reducing member 130 may be exposed from the distal opening of the lumen of the outer sheath 116 and extend in a distal direction out of the distal end of the outer sheath 116. The distance between the distal end of the friction-reducing member 130, and thus the distal end of the tethers 132, and the apertures 150 may be reduced as the outer sheath 116 is retracted proximally, thereby proximally retracting the distal end of the friction-reducing member 130 relative to the stent 128 to expose and thus unconstrain the stent 128 in a distal-to-proximal direction.

Figure 9:
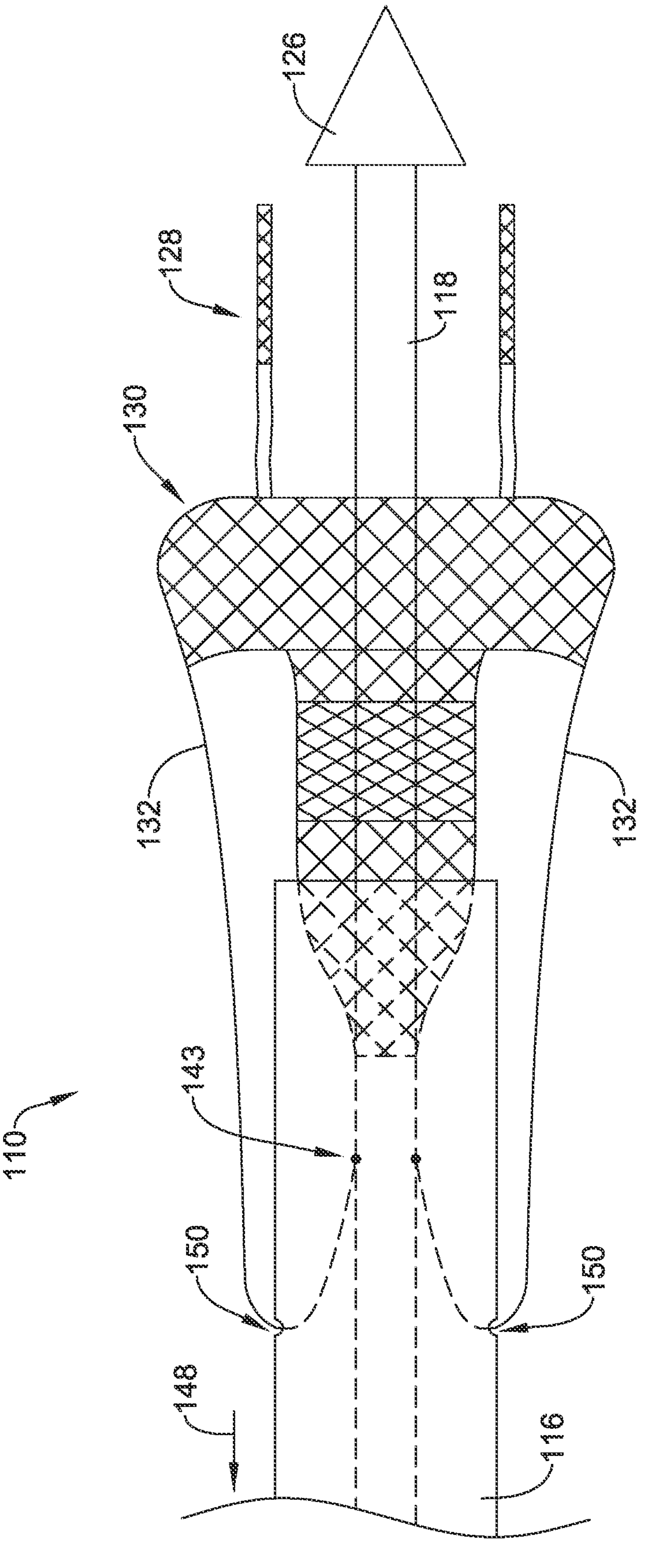
FIG. 9 illustrates another side view of the example stent delivery system shown in FIG. 8.

FIG. 9 illustrates the stent 128 after the outer sheath 116 has been further retracted in a proximal direction relative to the inner member 118 and the stent 128. It can be appreciated from FIG. 9 that as the outer sheath 116 is retracted proximally relative to the inner member 118 (while the inner member 118 remains stationary), the distance between the attachment point 143 and the apertures 150 increases. Further, as the distance between the attachment point 143 and the apertures 150 increases, it can be appreciated that more of the length of the tether members 132 is pulled through the apertures 150 and into the lumen of the outer sheath 116. In some instances, such as that shown in FIG. 9, as the outer sheath 116 is proximally retracted and, consequently, a greater amount of the length of each of the tether members 132 is drawn through the apertures 150 and into the outer sheath 116, the friction-reducing member 130 may continue to retract proximally (e.g., further fold back on itself (as shown in FIG. 9). Alternatively or additionally, in some examples, the delivery system 110 may be designed such that as the outer sheath 116 is proximally retracted and, consequently, a greater amount of the length of each of the tether members 132 is drawn through the apertures 150 and into the outer sheath 116, the friction-reducing member 130 may continue to longitudinally collapse (e.g., accordion) along its length.

Figure 10:
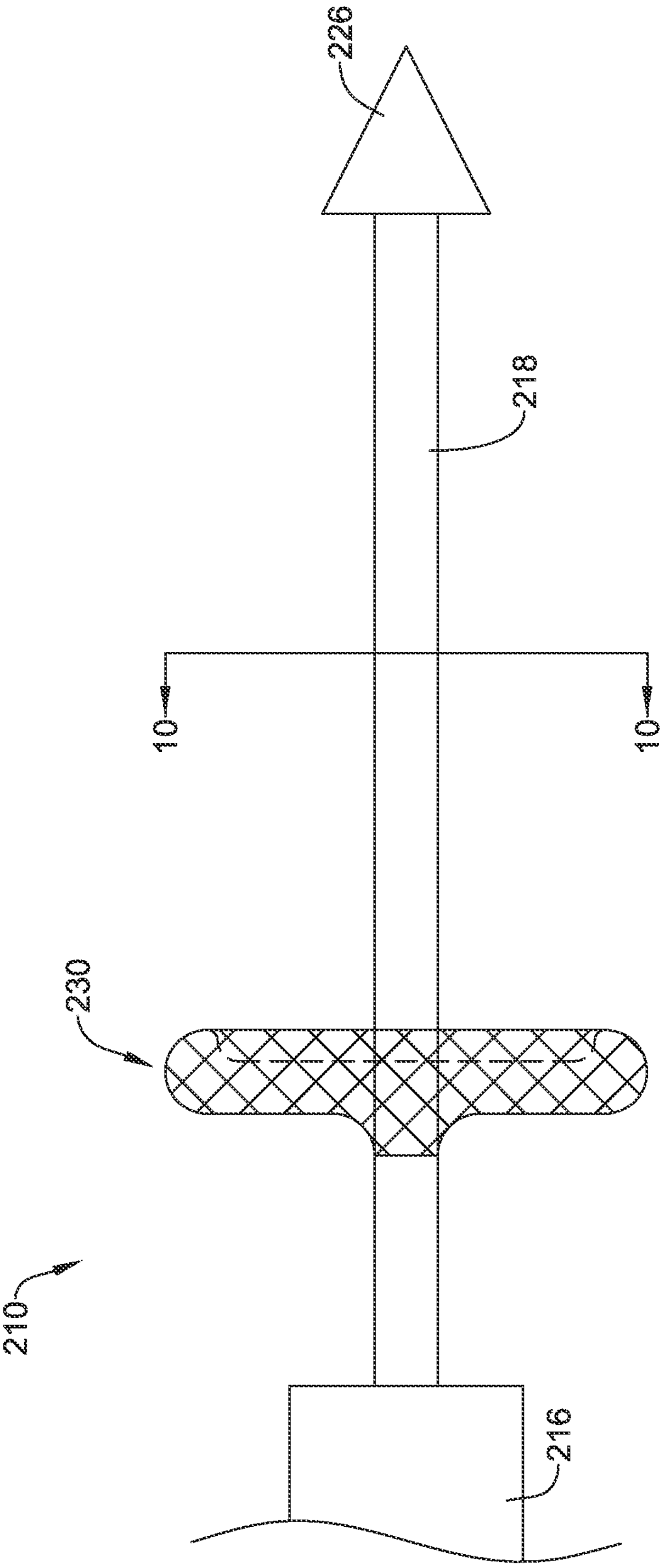
FIG. 10 illustrates a portion of another example stent delivery system.

FIG. 10 illustrates a portion of another example stent delivery system 210. For example, FIG. 10 illustrates an example inner member 218 extending through a lumen of an example outer sheath 216 and longitudinally moveable relative to the outer sheath 216. The inner member 218 and the outer sheath 216 may be similar in form and function as other inner members and outer sheaths described above. As shown in FIG. 10, the distal end of the inner member 218 may include or be coupled to a distal tip 226.

FIG. 10 further illustrates a friction reducing member 230 having its proximal end secured to the inner member 218. As an additional example to the friction-reducing members 30/130 described above, the friction reducing member 230 is illustrated in a proximally retracted, expanded configuration in which the distal end of the friction-reducing member 230 is retracted proximally toward the proximal end of the friction-reducing member 230. In some examples, the friction reducing member 230 illustrated in FIG. 10 may be heat set in the proximally retracted configuration, such as the shape shown in FIG. 10, thus defining an equilibrium configuration of the friction-reducing member 230. Additionally, unlike previous examples, the example friction-reducing member 230 illustrated in FIG. 10 does not include tether members attached thereto. Rather, the friction-reducing member 230 may be elongated distally and constrained over the length of a stent in an elongated, delivery configuration, with the outer sheath 216 constraining the friction-reducing member 230 in the elongated configuration. As the friction reducing member 230 is uncovered by and extends out of the distal end of the outer sheath 216 during deployment, the friction-reducing member 230 assumes its heat set configuration and shifts from its elongated, constrained configuration to the proximally retracted configuration illustrated in FIG. 10, thereby releasing the stent during deployment.

Figure 11:
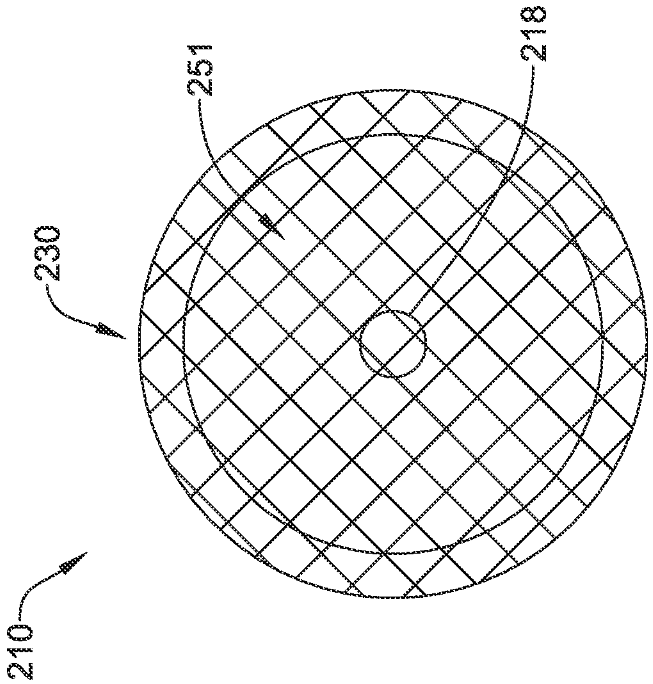
FIG. 11 illustrates an end view along line 10-10 of FIG. 10.

FIG. 11 illustrates an end view of the friction-reducing member 230 of the stent delivery system 210 taken along line 10-10 of FIG. 10. As shown in FIG. 11, the friction-reducing member 230 may be generally circular in shape. Additionally, the friction-reducing member 230 may include a receiving cavity 251 extending around the inner tubular member 218. This receiving cavity 251 may form a recessed area in which an example stent may be positioned.

Figure 12:
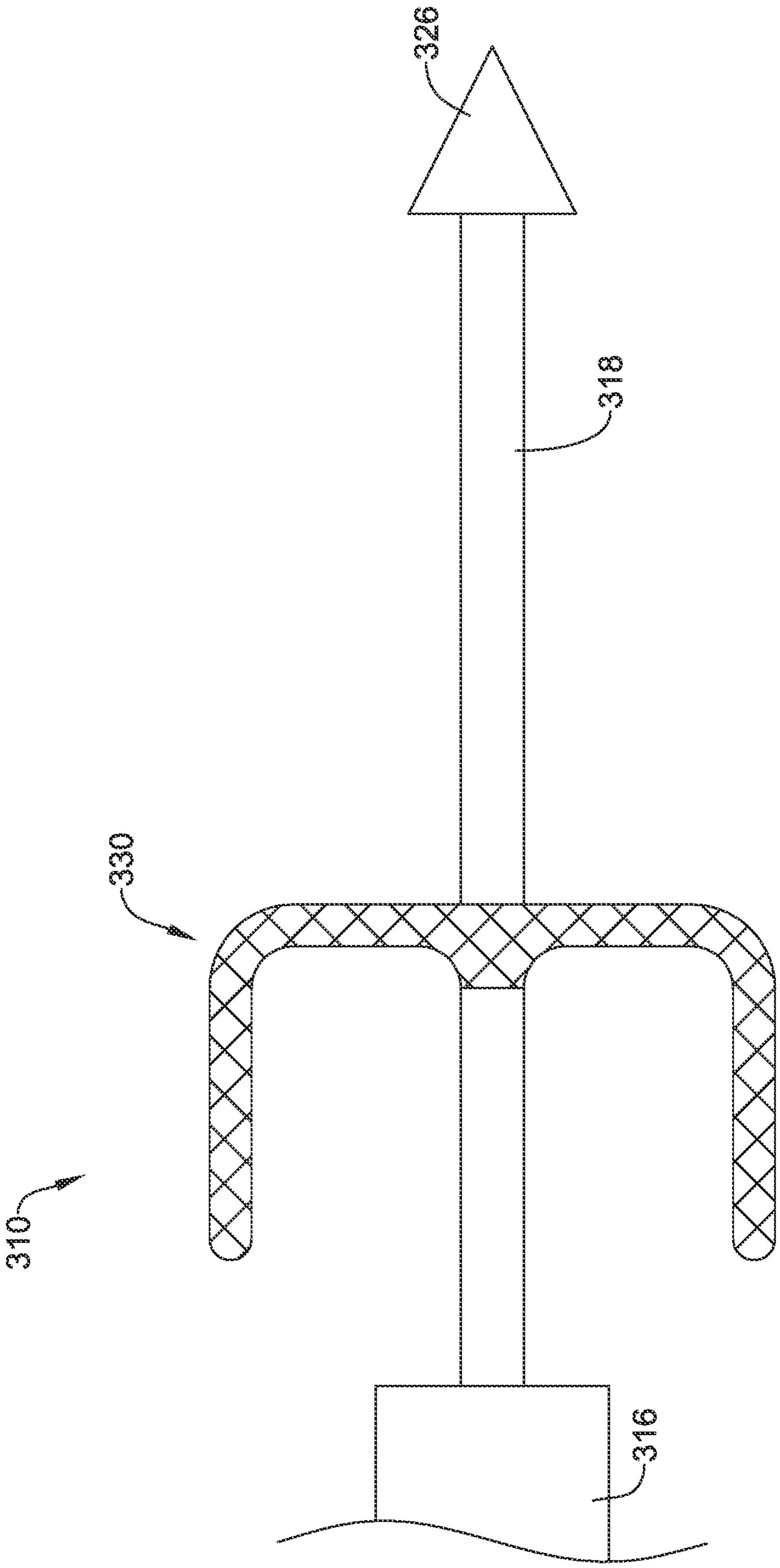
FIG. 12 illustrates a portion of another example stent delivery system.

FIG. 12 illustrates a portion of another example stent delivery system 310. For example, FIG. 12 illustrates an example inner member 318 extending through a lumen of an example outer sheath 316 and longitudinally moveable relative to the outer sheath 316. The inner member 318 and the outer sheath 316 may be similar in form and function as other inner members and outer sheaths described above. As shown in FIG. 12, the distal end of the inner member 318 may include or be coupled to a distal tip 326.

FIG. 12 further illustrates a friction reducing member 330 having its proximal end secured to the inner member 318. As an additional example to the friction-reducing members 30/130/230 described above, the friction-reducing member 330 is illustrated in a proximally retracted, expanded configuration in which the distal end of the friction-reducing member 330 is retracted proximal of the stent. In some examples, the friction-reducing member 330 illustrated in FIG. 12 may be heat set in the proximally retracted configuration, such as shape shown in FIG. 12, thus defining an equilibrium configuration of the friction-reducing member 330. Additionally, unlike previous examples, the example friction-reducing member 330 illustrated in FIG. 12 does not include tether members attached thereto. Rather, the friction-reducing member 330 may be elongated distally and constrained over the length of a stent in an elongated, delivery configuration, with the outer sheath 316 constraining the friction-reducing member 330 in the elongated configuration. As the friction-reducing member 330 is uncovered by and extends out of the distal end of the outer sheath 316 during deployment, the friction-reducing member 330 assumes its heat set configuration and shifts from its elongated, constrained configuration to the proximally retracted configuration illustrated in FIG. 12, thereby releasing the stent during deployment. In some instances, in the proximally retracted configuration, a portion of the friction-reducing member 330, such as a distal end region of the friction-reducing member 330 may extend proximal of the proximal end of the friction-reducing member 330 which is secured to the inner member 318. Thus, the distal end region of the friction-reducing member 330 may move from a location distal of the proximal end of the friction-reducing member 330 to a location proximal of the proximal end of the friction-reducing member 330 during proximal retraction of the outer sheath 316 during stent deployment.

Figure 13:
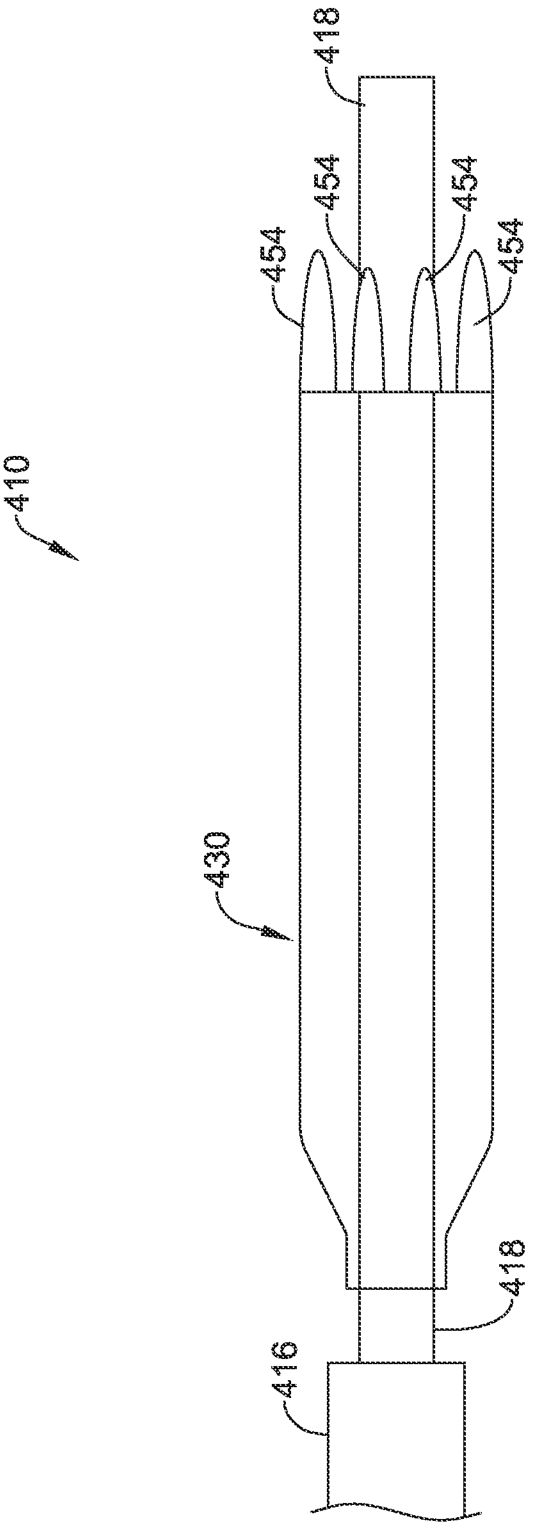
FIG. 13 illustrates a portion of another example stent delivery system.

FIG. 13 illustrates a portion of another example stent delivery system 410. For example, FIG. 13 illustrates an example inner member 418 extending through a lumen of an example outer sheath 416 and longitudinally moveable relative to the outer sheath 416. Further, FIG. 13 illustrates an example friction-reducing member 430 having its proximal end secured to the inner member 418. The inner member 418, the outer sheath 416 and the friction-reducing member 430 may be similar in form and function as the inner member 18, the outer sheath 16 and the friction-reducing member 30 described above.

However, as illustrated in FIG. 13, the stent delivery system 410 does not include a distal tip attached to or included with the inner member 418. Rather, FIG. 13 illustrates that the distal end of the friction-reducing member 430 includes or is attached to a plurality of tip segments 454. Each of the plurality of tip segments 454 has a first end attached to the distal end of the friction-reducing member and a second end which tapers to a generally narrowed shape. It can be appreciated that the tip segments 454 may be positioned around the circumference of the distal end of the friction-reducing member 430. Further, the plurality of tip segments 454 may be evenly spaced from one another.

Figure 14:
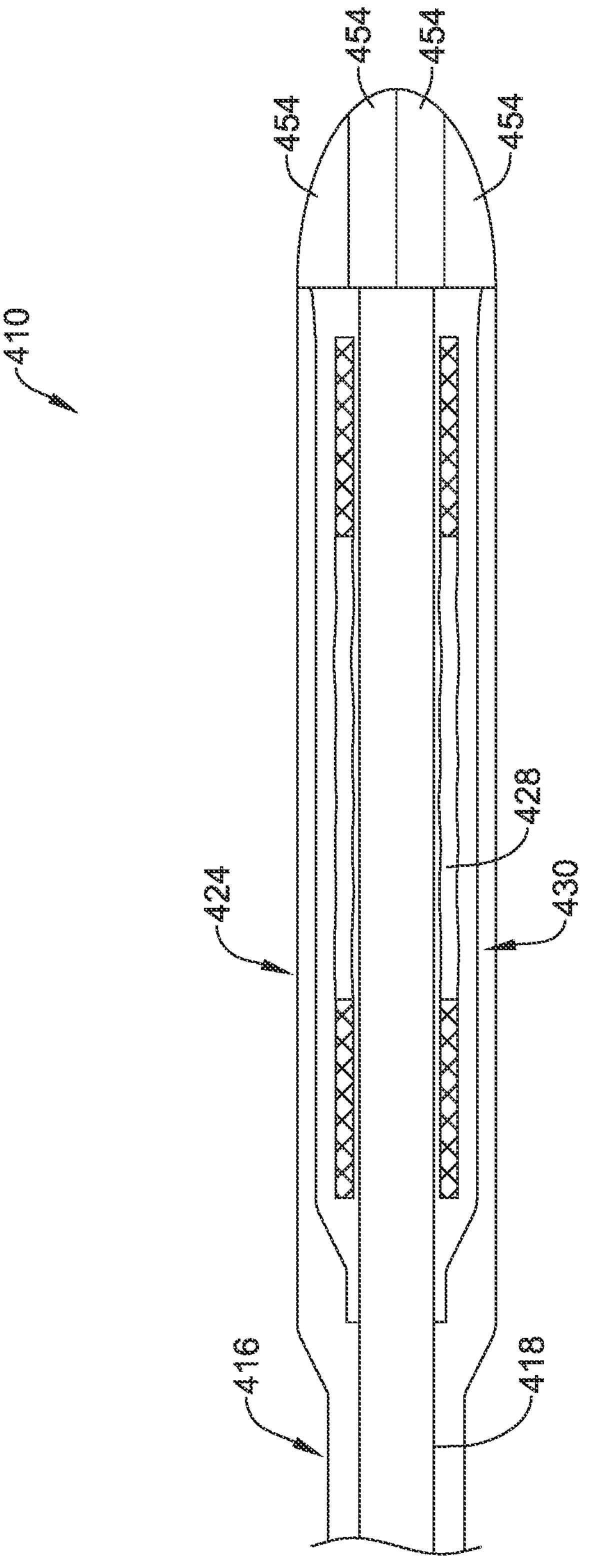
FIG. 14 illustrates a portion of another example stent delivery system.

FIG. 14 illustrates the stent delivery system 410 in a similar configuration to the stent delivery system 10 shown in FIG. 1. For example, FIG. 14 illustrates the stent 428 disposed along a stent receiving region of the inner member 418. Additionally, FIG. 14 shows the outer sheath 416 distally advanced over the friction-reducing member 430 to urge the friction-reducing member 430 into a radially collapsed and longitudinally extended configuration radially outward of the outer surface of the stent 428 and radially inward of the inner surface of the distal end region 424 of the outer sheath 416.

FIG. 14 further illustrates that when the friction-reducing member 430 is positioned in the radially collapsed and longitudinally extended configuration (such as that illustrated in FIG. 14), each of the plurality of tip segments 454 may converge and be positioned adjacent one another such that the plurality of tip segments collectively form a tapered distal tip extending distally from the distal end of the outer sheath 416.

The materials that can be used for the various components of system 10 (and/or other systems disclosed herein) may include those commonly associated with medical devices. However, this is not intended to limit the disclosure as the discussion may be applied to other similar members and/or components of members or systems disclosed herein.

The various components of system 10 (and/or other systems disclosed herein) may be made from a metal, metal alloy, polymer (some examples of which are disclosed below), a metal-polymer composite, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; iron, magnesium, manganese, platinum, chromium, nickel, cobalt, combinations thereof or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, various components of system 10 (and/or other systems disclosed herein) may also be doped with, made of, or otherwise include a radiopaque material including those listed herein or other suitable radiopaque materials.

In some embodiments, a degree of MRI compatibility is imparted into the various components of system 10 (and/or other systems disclosed herein). For example, to enhance compatibility with Magnetic Resonance Imaging (MRI) machines, it may be desirable to make the various components of system 10 (and/or other systems disclosed herein), in a manner that would impart a degree of MRI compatibility. For example, the various components of system 10 (and/or other systems disclosed herein), or portions thereof, may be made of a material that does not substantially distort the image and create substantial artifacts (artifacts are gaps in the image). Certain ferromagnetic materials, for example, may not be suitable because they may create artifacts in an MRI image. The various components of system 10 (and/or other systems disclosed herein), or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be used to form various components of system 10 (and/or other systems disclosed herein) may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), poly-L-lactic acid (PLLA), poly-D-lactic acid (PDLA), poly-lactic acid (PLA), poly(lactic-co-glycolic acid) (PLGA), poly(ε-caprolactone) (PCL), desaminotyrosine polycarbonate and the like, polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6% LCP.

In some embodiments, the various components of system 10 (and/or other systems disclosed herein) may include a coating, for example a lubricious, a hydrophilic, a protective, or other type of coating. Hydrophobic coatings such as fluoropolymers provide a dry lubricity which improves device handling and exchanges. Lubricious coatings improve steerability and improve lesion crossing capability. Suitable lubricious polymers may include silicone and the like, polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, the entire disclosures of which are incorporated herein by reference.

In at least some examples, the various components of system 10 disclosed herein may include a metal stent, a bioabsorbable metal stent, a drug coated metal stent, a drug coated bioabsorbable metal stent, a polymeric stent, a bioabsorbable polymeric stent, a drug coated polymeric stent, a drug coated bioabsorbable polymeric stent, or the like. Some examples of suitable drugs and/or therapeutic agents that may be used with the medical device contemplated herein may include paclitaxel and/or derivatives thereof, everolimus and/or derivatives thereof (e.g., the "limus" family of drugs), combinations thereof, and the like, or other suitable materials.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. A stent delivery system, comprising:

an outer shaft having a distal end, a proximal end, and an inner surface defining a lumen extending therein;

an inner shaft extending at least partially within the lumen of the outer shaft, the inner shaft having a stent receiving region disposed adjacent a distal end region thereof;

a stent disposed along the stent receiving region; and a friction-reducing member positioned between an outer surface of the stent and the inner surface of the outer shaft, the friction-reducing member having a proximal end attached to the inner shaft proximal of the stent and a distal end coupled to the outer shaft distal of the stent, the friction-reducing member exerting a radially inward compressive force along the stent, wherein when the outer shaft is withdrawn proximally, a single layer of the friction-reducing member forms a longitudinally collapsed and radially expanded region in which an outer diameter of the single layer increases and a length of the single layer reduces as the outer shaft moves proximally;

wherein the outer shaft defines an outermost wall of the stent delivery system extending from a handle coupled to the proximal end of the outer shaft to distal of the stent when in a delivery configuration.

2. The stent delivery system of claim 1, wherein the longitudinally collapsed and radially expanded region is formed proximal of the distal end of the friction-reducing member.

3. The stent delivery system of claim 1, wherein as the outer shaft is moved proximally, the distal end of the friction-reducing member forms a rolled-back region, wherein the longitudinally collapsed and radially expanded region is formed proximal of the rolled-back region.

4. The stent delivery system of claim 1, wherein the friction-reducing member is configured to space the inner surface of the outer shaft radially away from the outer surface of the stent.

5. The stent delivery system of claim 1, wherein retraction of the outer shaft uncovers at least a portion of the friction-reducing member, and wherein the uncovered portion of the friction-reducing member expands radially outward as the outer shaft is retracted.

6. The stent delivery system of claim 5, wherein the uncovered portion of the friction-reducing member includes a flared region tapering outward to a larger diameter in a distal direction.

7. The stent delivery system of claim 6, wherein the larger diameter is greater than an outer diameter of the outer shaft.

8. The stent delivery system of claim 1, wherein the friction-reducing member is braided.

9. The stent delivery system of claim 1, further comprising a plurality of tether members each having a first end directly coupled to the friction-reducing member and a second end directly coupled to the outer shaft.

10. The stent delivery system of claim 9, wherein retraction of the outer shaft retracts the plurality of tether members in a proximal direction, and wherein retraction of the tether members folds the friction-reducing member back on itself.

11. A stent delivery system, comprising:

an outer shaft having a distal end, a proximal end, and an inner surface defining a lumen extending from the distal end to the proximal end;

an inner shaft extending at least partially within the lumen of the outer shaft, the inner shaft having a stent receiving region disposed along a distal end region thereof, wherein the inner shaft is designed to translate longitudinally relative to the outer shaft;

a self-expanding stent disposed along the stent receiving region;

a friction-reducing sleeve positioned between an outer surface of the stent and the inner surface of the outer shaft, the friction-reducing sleeve having a proximal end attached to the inner shaft proximal of the stent and a distal end coupled to the outer shaft distal of the stent, wherein as the outer shaft is moved proximally, the distal end of the friction-reducing sleeve forms a rolled-back region, wherein the friction-reducing sleeve forms a longitudinally collapsed and radially expanded region in which an outer diameter increases and a length reduces as the outer shaft moves proximally, wherein the longitudinally collapsed and radially expanded region is formed proximal of the rolled-back region; and one or more tether members coupled to the friction-reducing sleeve and extending therefrom, wherein longitudinal retraction of the outer shaft relative to the inner shaft exposes the stent from the friction-reducing sleeve.

12. The stent delivery system of claim 11, wherein retraction of the outer shaft uncovers at least a portion of the friction-reducing sleeve, and wherein the uncovered portion of the friction-reducing sleeve expands radially outward as the outer shaft is retracted.

13. The stent delivery system of claim 12, wherein the uncovered portion of the friction-reducing sleeve includes a flared region tapering outward to a larger diameter in a distal direction.

14. The stent delivery system of claim 13, wherein the larger diameter is greater than an outer diameter of the outer shaft.

15. The stent delivery system of claim 11, wherein the friction-reducing sleeve is braided.

16. The stent delivery system of claim 11, wherein the outer shaft defines an outermost wall of the stent delivery system extending from a handle coupled to the proximal end of the outer shaft to distal of the stent when in a delivery configuration.

17. A stent delivery system, comprising:

an outer shaft having a distal end, a proximal end, and an inner surface defining a lumen extending therein;

an inner shaft extending at least partially within the lumen of the outer shaft, the inner shaft having a stent receiving region disposed adjacent a distal end region thereof;

a stent disposed along the stent receiving region; and a braided friction-reducing member positioned between an outer surface of the stent and the inner surface of the outer shaft, the friction-reducing member having a proximal end attached to the inner shaft proximal of the stent and a distal end coupled to the outer shaft distal of the stent, wherein proximal retraction of the outer shaft uncovers at least a portion of the friction-reducing member, and the uncovered portion of the friction-reducing member forms a radially outward expanded portion as the outer shaft is retracted, wherein an outer diameter of the radially outward expanded portion of the friction-reducing member is greater than an outer diameter of the outer shaft;

wherein the outer shaft defines an outermost wall of the stent delivery system extending from a handle coupled to the proximal end of the outer shaft to distal of the stent when in a delivery configuration;

wherein as the outer shaft is retracted proximally, the distal end of the friction-reducing member forms a rolled-back region, wherein the friction-reducing member forms a longitudinally collapsed and radially expanded region in which an outer diameter increases and a length reduces as the outer shaft moves proximally, wherein the longitudinally collapsed and radially expanded region is formed proximal of the rolled-back region.

* * * * *